United States Patent [19]

Franz

[11] 4,131,448

[45] Dec. 26, 1978

[54] N-ORGANO-N-PHOSPHONOMETHYLGLYCINE-N-OXIDES AND PHYTOTOXICANT COMPOSITIONS CONTAINING SAME

[75] Inventor: John E. Franz, Crestwood, Mo.

[73] Assignee: Monsanto Company, St. Louis, Mo.

[21] Appl. No.: 836,338

[22] Filed: Sep. 26, 1977

Related U.S. Application Data

[60] Continuation-in-part of Ser. No. 613,708, Sep. 9, 1975, Pat. No. 4,062,669, which is a division of Ser. No. 313,706, Dec. 11, 1972, abandoned.

[51] Int. Cl.² ............................................. A01N 9/36
[52] U.S. Cl. ..................................................... 71/86
[58] Field of Search ........................... 71/86, 121, 94; 260/502.5

[56] References Cited

U.S. PATENT DOCUMENTS

| | | | |
|---|---|---|---|
| 3,429,914 | 2/1969 | Crutchfield et al. | 260/502.5 |
| 3,439,018 | 4/1969 | Brookes et al. | 71/118 |
| 3,455,675 | 7/1969 | Irani | 71/86 |
| 3,459,759 | 8/1969 | Rochling et al. | 71/94 |
| 3,556,762 | 1/1971 | Hamm | 71/86 |
| 3,697,251 | 10/1972 | Long et al. | 71/94 |
| 4,002,672 | 1/1977 | Smith | 71/86 |
| 4,062,669 | 12/1977 | Franz | 71/86 |

*Primary Examiner*—Glennon H. Hollrah
*Attorney, Agent, or Firm*—Arnold H. Cole; Donald W. Peterson

[57] ABSTRACT

This disclosure relates to N-organo-N-phosphonomethylglycine-N-oxides and derivatives thereof, to processes for producing same, and to herbicidal compositions and herbicidal methods. These compounds and the compositions containing them are useful as phytotoxicants or herbicides.

16 Claims, No Drawings

N-ORGANO-N-PHOSPHONOMETHYLGLYCINE-N-OXIDES AND PHYTOTOXICANT COMPOSITIONS CONTAINING SAME

This is a continuation-in-part of application Ser. No. 613,708, filed Sept. 9, 1975, now U.S. Pat. 4,062,669, which is in turn a division of application Ser. No. 313,706, filed Dec. 11, 1972, and now abandoned.

This invention relates to novel N-organo-N-phosphonomethylglycine-N-oxides and to methods for their preparation. These N-organo-N-phosphonomethylglycine-N-oxides are useful as herbicides or phytotoxicants. This invention further relates to phytotoxicant compositions and to herbicidal methods.

The term "phytotoxicant" as used herein means materials which (1) effectively control all plants in a given locus or (2) selectively control the growth of one or more plant species in the presence of other plants. In like manner, "phytotoxic" and "phytotoxicity" are used to identify the overall and selective control activity of the compounds and compositions of this invention. The term "control" as used herein is inclusive of the actions of (1) killing, (2) inhibiting growth, reproduction or proliferation, and (3) removing, destroying or otherwise diminishing the occurrence and activity of plants and is applicable to any of the stated actions, or any combination thereof.

The term "plant" as used herein means terrestrial plants and aquatic plants.

The term "terrestrial plant" is inclusive of germinating seeds, emerging seedlings and herbaceous vegetation including the roots and above-ground portions, as well as established woody plants.

The term "aquatic plant" means algae and higher aquatic plants. The term "higher aquatic plant" means aquatic plants which are botanically higher than algae and is inclusive of vegetative organisms growing in water in which a major part of such organisms are normally largely submerged, e.g. roots as in Lemna, leaves as in Vallisneria or entire plants such as Anacharis. Thus, the term "higher aquatic plant" is inclusive of all water plants whether normally free-floating in their environing water such as Salvinia, or immersed species which are normally rooted in soil such as Vallisneria, as well as species which appear to grow normally in all respects either free-floating or rooted such as Anacharis or Alternanthera.

The N-organo-N-phosphonomethylglycine-N-oxides of this invention are those having the formula

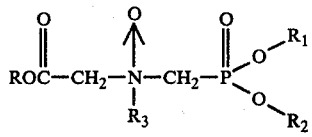

wherein R, $R_1$ and $R_2$ are each independently selected from the group consisting of hydrogen, monovalent hydrocarbon groups each containing from 1 to 10 carbon atoms, halogenated monovalent hydrocarbon groups containing from 1 to 10 carbon atoms and from 1 to 3 halogen substituents, monovalent hydrocarbonoxyhydrocarbon groups each containing from 1 to 10 carbon atoms and salt-forming alkali or alkaline earth metal cations, ammonium and organic ammonium groups and $R_3$ is a monovalent organic groups selected from the class consisting of aliphatic hydrocarbon groups containing from 1 to 18 carbon atoms and hydrocarbonoxyalkyl groups containing from 1 to 18 carbon atoms, and aliphatic hydrocarbon groups substituted with halogen, carboxyl, carboalkoxy, cyano, nitro, alkoxy, aryloxy, alkyl, aryl or heterocyclic groups and

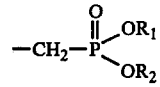

groups wherein $R_1$ and $R_2$ are as hereinbefore defined. The herbicidally active compounds are those wherein at least one of the $R_1$ or $R_2$ groups in the molecule is other than a monovalent hydrocarbon, monovalent hydrocarbonoxyhydrocarbon, or heterocyclic group, i.e., a hydrogen or a cation.

In accordance with the process of this invention, the N-oxides of formula (I) are produced by the following general procedure:

A mixture of an N-organo-N-phosphonomethylglycine having the formula

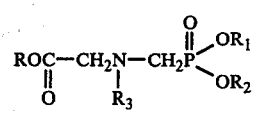

wherein R, $R_1$, $R_2$ and $R_3$ are as above defined and can be oxidized to the corresponding N-oxide under acidic or basic conditions. In the acidic method the phosphonomethylglycine is suspended or dissolved in a suitable acid (i.e. acetic, trifluoroacetic, dilute sulfuric, etc.) and hydrogen peroxide or other oxidizing agent is added dropwise at a suitable temperature (0°–100° C., preferably 30°–80° C.). The reaction is exothermic and in some media (acetic or trifluoroacetic acid), the N-oxide precipitates as a white solid. In other instances, (dilute sulfuric acid) the product remains dissolved and is recovered by concentration and dilution with an appropriate solvent (e.g. ethanol).

The alkaline method is carried out by neutralizing all acidic functions of the N-organo-N-phosphonomethylglycine with strong aqueous alkali followed by addition of hydrogen peroxide or other oxidizing agent at a suitable temperature (0°–100° C., preferably 20°–60° C.). The alkali salt of the N-oxide which forms is soluble in the reaction medium and is generally recovered by concentration at reduced pressure or is precipitated by the addition of a suitable solvent.

It is believed that the reaction proceeds in accordance with the following equation which, for convenience, shows the oxidation of N-phosphonomethylimino diacetic acid in an acidic medium:

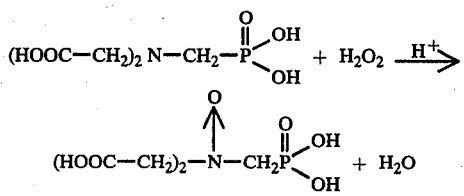

It will, of course, be apparent to those of ordinary skill in the art that the salts can then be obtained by reaction with the proper base.

The ratio of reactants employed in the process of this invention is not narrowly critical. It is obvious to those skilled in the art that for best yields one must employ at least one mole of hydrogen peroxide for each mole of the N-organo-N-phosphonomethylglycine reactant. For best results, it is preferred to employ from two to three moles of hydrogen peroxide for each mole of the N-organo-N-phosphonomethylglycine reactant.

The temperature at which the process of this invention is conducted is not narrowly critical and can range from 0°–100° C. It has been found that if the temperature is too high, then the N-oxide produced decomposes, yielding a mixture of starting material and decomposition products. It is preferred in most instances to conduct the process of this invention in the range of from 25°–80° C. in order to obtain the best yields of the N-oxide product and avoid its decomposition.

The oxidizing agents which can be employed in the process of this invention include inorganic peroxides such as hydrogen peroxide, sodium peroxide, potassium peroxide, lithium peroxide, cesium peroxide and the like; persulfuric and perboric acid and the salts of these per acids such as the sodium, lithium and potassium persulfates and perborates; peroxy organic acids and their salts such as, for example, peroxy acetic acid, peroxybenzoic acid, m-chloroperoxybenzoic acid, 2,4-dichloroperoxybenzoic acid, peroxyformic acid, peroxytrifluoroacetic acid and the like; organic peroxides such as benzoyl peroxide, etc. and ozone.

Inasmuch as the reaction in the process of this invention is exothermic, it is preferred to employ a solvent to aid in the dissipation of the heat of reaction and to bring the reactants into more intimate contact. Solvents which can be employed in the process of this invention are those that do not react substantially with the oxidizing agent or the N-organo-N-phosphonomethylimino acetic acid reactants under the conditions employed. Such solvents are, for example, water, liquid acids such as acetic acid, trifluoro acetic acid, formic acid, propionic acid, sulfuric acid and the like; alcohols such as methanol, ethanol, isopropanol, carbitol, methyl cellosolve and the like; ethers such as dioxane, tetrahydrofuran, dimethyl ethers of ethylene glycol, diethylene glycol dimethyl ether and the like; sulfones such as sulfolane and the like, ketones such as acetone and nitriles such as acetonitrile.

The process of this invention can be conducted at atmospheric pressure, sub-atmospheric pressure or super-atmospheric pressure. For convenience and economy, it is generally preferred to conduct the process of this invention at atmospheric pressure.

The term halogen as employed herein means chlorine, bromine, iodine and fluorine.

The term monovalent hydrocarbon as used herein includes alkyl, alkenyl, alkynyl, and aralkyl inclusive of both straight and branched chain radicals, such as methyl, ethyl, isopropyl, cyclopropyl, cyclohexyl, tertiary butyl, n-butyl and the various isomers of amyl, hexyl, heptyl, octyl, nonyl, decyl, undecyl, dodecyl, tridecyl, tetradecyl, pentadecyl, hexadecyl, heptadecyl, octadecyl, benzyl, phenylethyl, naphthylethyl, tolylethyl, methylbenzyl, phenylbenzyl, and the corresponding alkenyl, and alkynyl groups and the like; aryl groups and alkaryl groups such as phenyl, tolyl, xylyl, naphthyl, vinylphenyl and the like.

The monovalent hydrocarbonoxyhydrocarbon groups represented by R, $R_1$, $R_2$ and $R_3$ include alkoxyalkyl, alkenoxyalkyl, alkoxyalkoxyalkyl, alkenoxyalkoxyalkyl, dialkoxyalkyl, alkenoxy(alkoxy)alkyl, alkenoxyalkoxy(alkoxy)alkyl, alkoxyalkoxy(alkoxy)alkyl, aryloxyalkyl and alkoxyaryl such as 2-methoxyethyl, 4-ethoxy-2-methylbutyl, 2-ethoxyethyl, 3-propoxypropyl, 4-methoxybutyl, 4-methoxy-2-ethylbutyl, 4-butoxybutyl, 2-allyloxyethyl, 2-butenoxyethyl, 4-butenoxybutyl, 2-(2-methoxyethoxy)ethyl, 2-(2-butoxyethoxy)ethyl, 4-(3-methoxypropoxy)butyl, 2-(3-allyloxypropoxy)ethyl, 2-(2-butenoxyethoxy)ethyl, phenoxyethyl, naphthoxyethyl, tolyloxyethyl, 4-phenoxybutyl and the like. R, $R_1$ and $R_2$ can also be trifluoromethylphenyl, ethoxyphenyl, methoxyphenyl, chlorophenyl and the like.

Illustrative of the halogenated monovalent hydrocarbon groups represented by R, $R_1$, $R_2$ and $R_3$ are haloalkyl such as chloromethyl, iodomethyl, bromomethyl, fluoromethyl, chloroethyl, iodoethyl, bromoethyl, 1,2-dichloroethyl, 1,2-diiodoethyl, 2,2-dibromoethyl, chloro-n-propyl, bromo-n-propyl, iodoisopropyl, bromo-n-butyl, bromo-tert-butyl, 1,3,3-trichlorobutyl, 1,3,3-tribromobutyl, chloropentyl, bromopentyl, 2,3-dichloropentyl, 3,3-dibromopentyl, chlorohexyl, bromohexyl, 2,4-dichlorohexyl, 1,3-dibromohexyl, 1,3,4-trichlorohexyl, chloroheptyl, bromoheptyl, fluoroheptyl, 1,3-dichloroheptyl, 1,4,4-trichloroheptyl, 2,4-dichloromethylheptyl, chlorooctyl, bromooctyl, iodooctyl, 2,4-dichloromethylhexyl, 2,4-dichlorooctyl, 2,4,4-trichloromethylpentyl, 1,3,5-tribromooctyl and the halogenated straight and branched chain nonyl, decyl, undecyl, dodecyl, tridecyl, tetradecyl, pentadecyl, hexadecyl, heptadecyl and octadecyl; haloalkenyl such as chlorovinyl, bromovinyl, chloroallyl, bromoallyl, 3-chloro-n-butenyl-1, 3-chloro-n-pentenyl-1, 4-chloro-n-hexenyl-2, 3,4-dichloromethylpentenyl-1, 3-fluoro-n-heptenyl-1, 1,3,3-trichloro-n-heptenyl-5, 1,3,5-trichloro-n-octenyl-6, 2,3,3-trichloromethylpentenyl-4 and the various homologues and isomers of haloalkenyl having 2 to 12 carbon atoms. Illustrative of the haloaryl groups represented by R, $R_1$ and $R_2$ are o-chlorophenyl, m-chlorophenyl, m-bromophenyl, p-chlorophenyl, 2,4-dichlorophenyl, 3,5-dichlorophenyl, 2,5-diiodophenyl and the like. The halogenated monovalent hydrocarbonoxyhydrocarbon groups represented by $R_3$ are the alkoxy and aryloxy substituted derivatives of the foregoing halogenated monovalent hydrocarbon groups where the alkyl groups are those previously set forth.

Illustrative of the heterocyclic groups which are substituted on the aliphatic group represented by $R_3$ are, for example, piperazinyl, quinolinyl, pyridinyl, morpholinyl, piperidinyl, pyrrolidinyl, indolinyl, azepinyl, furyl, thienyl, thenyl, furfuryl and the like.

The term "alkali-metal" encompasses lithium, sodium, potassium, cesium and rubidium; and the term "alkaline earth metal" includes beryllium, magnesium, calcium, strontium and barium.

The organic ammonium salts of the above formula are those prepared from low molecular weight organic amines, i.e. having a molecular weight below about 300, and such organic amines include the alkyl amines, alkylene amines and alkanol amines containing not more than 2 amine groups, such as methylamine, ethylamine, n-propylamine, isopropylamine, n-butylamine, isobutylamine, sec-butylamine, n-amylamine, iso-amylamine, hexylamine, heptylamine, octylamine, nonylamine, decylamine, undecylamine, dodecylamine, tridecylamine, tetradecylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, diisopropylamine, di-n-amylamine, diisoamylamine, dihexylamine, di-heptylamine, dioctylamine, trimethylamine, triethylamine, tri-n-propylamine, triisopropylamine, tri-n-butylamine, triisobutylamine, tri-sec-butylamine, tri-n-amylamine, ethanolamine, n-propanolamine, isopropanolamine, diethanolamine, N,N-diethylethanolamine, N-ethylpropanolamine, N-butylethanolamine, allylamine, n-butenyl-2-amine, n-pentenyl-2-amine, 2,3-dimethylbutenyl-2-amine, di-butenyl-2-amine, n-hexenyl-2-amine and propylenediamine, primary aryl amines such as aniline, methoxyaniline, ethoxyaniline, o,m,p-toluidine, phenylenediamine, 2,4,6-tribromoaniline, benzidine, naphthylamine, o,m,p-chloroaniline, and the like; heterocyclic amines such as pyridine, morpholine, piperidine, pyrrolidine, indoline, azepine piperazine, quinoline and the like.

Among the preferred biologically active compounds of this invention are those of the formula

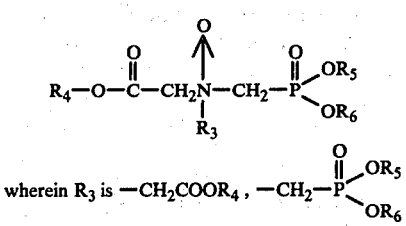

wherein $R_3$ is $-CH_2COOR_4$, $-CH_2-P\overset{O}{\underset{}{\diagdown}}\genfrac{}{}{0pt}{}{OR_5}{OR_6}$ or an alkyl group of from 1 to 12 carbon atoms; $R_4$ is hydrogen, lower alkyl or a salt-forming cation, $R_5$ and $R_6$ are each independently hydrogen, a salt-forming cation, ammonium or organic ammonium. The more preferred compounds are those wherein at least one of $R_4$, $R_5$ and $R_6$ is a salt-forming cation and the remainder are hydrogen.

The compounds of this invention wherein R, $R_1$ and $R_2$ are monovalent hydrocarbon groups have only mild or no herbicidal activity; however, these groups can be partially hydrolyzed in basic aqueous media to yield salts which are useful as herbicides.

The salts of N-organo-N-phosphonomethylglycine-N-oxides are prepared by partial or complete neutralization of the acid with the appropriate base, basic carbonate, ammonia or organic amine.

In accordance with this invention, it has been found that the growth of germinating seeds, emerging seedlings, maturing and established woody and herbaceous vegetation and aquatic plants can be controlled by exposing the emerging seedlings or above-ground portions of maturing and established vegetation, or the aquatic plants to the action of an effective amount of the N-organo-N-phosphonomethylglycine-N-oxides of the present invention. The compounds can be used individually, as admixtures of two or more compounds, or in admixture with an adjuvant. These compounds are effective as post-emergent phytotoxicants or herbicides, e.g., the selective control of the growth of one or more monocotyledonous species and/or one or more dicotyledonous species in the presence of other monocotyledons and/or dicotyledones. Furthermore, these compounds are characterized by broad spectrum activity, i.e., they control the growth of a wide variety of plants including, but not limited to, ferns, conifer (pine, fir and the like), aquatic, monocotyledons and dicotyledons.

The instant application is particularly directed to herbicidal compositions containing a compound of the formula

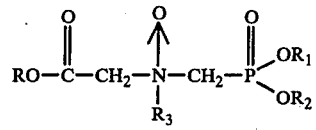

wherein $R_1$ and $R_2$ are each independently selected from the group consisting of hydrogen, salt forming alkali or alkaline earth metal cations, ammonium or organic ammonium groups, said organic ammonium group being derived from an organic amine having a molecular weight below about 300 and containing not more than two amine groups, R is selected from the same group as $R_1$ plus lower alkyl, and $R_3$ is selected from the group consisting of alkyl of 1 to 12 carbon atoms, allyl, cyclohexyl, phenalkyl and phenoxyalkyl of 7 to 8 carbon atoms, and the mono and dihalogenated derivatives of such alkyl, allyl, cyclohexyl, phenalkyl and phenoxyalkyl.

In the following examples, which illustrate the invention, and throughout the specification, parts and percent are by weight unless otherwise indicated.

EXAMPLE 1

A mixture of 2.3 grams (0.01 mole) of N-phosphonomethylimino diacetic acid, 7 mls. of trifluoroacetic acid and 9 mls. of 30% hydrogen peroxide (0.08 mole) were charged into a pyrex glass reaction vessel. The mixture was heated and at about 55° C. a reaction appeared to begin. The temperature rose to 65° C. at which point the mixture was clear and vigorous gas evolution took place. The temperature was maintained at about 50°–60° C., until precipitation of a white solid appeared complete. The mixture was cooled to room temperature (at 25° C.) and stored for about 72 hours. The white solid was then collected, washed with ethanol and ether and air dried. Approximately 2.0 grams of the white solid was obtained. The white solid which was water soluble, melted at 149° C. with decomposition, slowly liberating iodine from a sodium iodide solution, was identified as N-phosphonomethyliminodiacetic acid-N-oxide by elemental analysis, infrared and nuclear magnetic resonance spectral analysis. A sample recrystallized from tetrahydrofuran had a melting point of 146.5° C. with decomposition, and gave the following analysis:

Calculated: C, 24.70%; H, 4.15%; N, 5.76%; P, 12.74% Found: C, 24.61%; H, 4.21%; N, 5.64%; P, 12.70%

EXAMPLE 2

A mixture of N-phosphonomethylimino diacetic acid (13.7 grams, 0.06 moles), 100 mls. of glacial acetic acid and 0.6 grams of concentrated sulfuric acid were placed in a 250 ml. pyrex flask, fitted with stirrer, condenser and thermometer. The mixture was stirred at 75°–80° C. while 24 ml. (0.21 moles) of 30% hydrogen peroxide was added dropwise over 25 minutes. Gas slowly evolved, the rate becoming faster as the addition progressed. The mixture took on a milky appearance and the solid material was replaced by a colloid. The reaction mixture was then stirred at 80° C. for 1 hour. Approximately 50 minutes after the addition was complete, the precipitation of a granular solid began. The mixture was stirred at 75° C. for an additional hour and a sample of the solid removed, washed with ethanol and diethyl ether and analyzed by nuclear magnetic resonance spectra. The spectra indicated that none of the starting material was present in the reaction mixture. The reaction mixture was then cooled in a refrigerator, the solid collected, washed with glacial acetic acid, ethanol and ether and then air dried. A white solid (9.2 grams) having a melting point of 152° C. with decomposition, which was identified as N-phosphonomethylimino diacetic acid-N-oxide was obtained.

EXAMPLE 3

A mixture of N-methyl-N-phosphonomethyl glycine (9.2 grams, 0.05 mole), 25 ml. of water and 6 grams (0.15 mole) of sodium hydroxide was stirred at 35° C. as 6 ml. of 30% hydrogen peroxide (0.05 mole) was added in one portion. An exothermic reaction occurred and the temperature rose to 50° C. at which point water cooling was applied. Gas evolution also occurred during this period. After a short time, the gas evolution ceased and the cooling means was removed. The temperature began to slowly drop. The reaction solution was concentrated at 20 mm. of mercury with warming to remove the majority of the water. The residue was then concentrated at 0.5 Torr and finally dried in a desiccator for four days. The yield of the white solid was 15.9 grams. The material was further dried in the desiccator at which time the weight decreased to 14 grams. The material was identified as a dihydrate of the trisodium salt of the N-oxide of N-methyl-N-phosphonomethyl glycine, m.p. 135° C. (dec), and gave the following analysis:

Calculated: C, 15.96%; H, 3.68%; N, 4.65%; Na, 22.91% Found: C, 15.82%; H, 3.73%; N, 4.70%; Na, 22.54%

EXAMPLE 4

A mixture of N,N-bis(phosphonomethyl) glycine (26.3 grams, 0.10 mole), 30 ml. of water and sodium hydroxide (20 grams, 0.5 mole) was stirred at 70° C. and then cooled to 30° C. to form the pentasodium salt. At this point, hydrogen peroxide (30%, 12 grams, 0.11 mole) was added to one portion. The material began to heat up and as the temperature rose to 52° C., external heating was stopped for 10 minutes at which time the reaction mixture began to cool. The mixture was then heated at 54°-55° C. for an additional two and one half hours. Seventy mls. of a viscous colorless solution weighing 96.1 grams was obtained. A portion of this solution (10.9 grams) was concentrated at reduced pressure (20 Torr) while gently warming on a steam bath. The residue (6.7 grams) was then further evacuated with warming at 0.5 Torr until a weight of 5.8 grams was obtained. A final drying at 0.5 Torr in a desiccator was carried out for one day. The weight of the residue obtained was 5.2 grams. The white solid gave the following elemental analysis:

Calculated: C, 10.42%; H, 3.06%; N, 3.04% Found: C, 10.35%; H, 3.25%; N, 3.03%

This corresponds to the pentasodium salt of N,N-bis(-phosphonomethyl)glycine-N-oxide tetrahydrate.

EXAMPLE 5

A mixture of N-phosphonomethyliminodiacetic acid (23 grams, 0.1 mole), water (100 mls.), sodium hydroxide (16 grams, 0.40 moles) and 30% hydrogen peroxide (12 grams, 0.11 mole) was warmed with stirring to 40° C. The reaction mixture was then heated to about 50° C. for approximately 7 hours. The reaction mixture was allowed to cool overnight and then concentrated under reduced pressure with gentle warming until a viscous residue remained. This viscous residue was further concentrated at 0.5 Torr overnight and then dried in a desiccator at 0.5 Torr for 6 days. A white solid material weighing 36.3 grams was obtained. This material was identified as the tetrasodium salt of N-phosphonomethylimino diacetic acid-N-oxide dihydrate and had the following elemental analysis:

Calculated: C, 16.36%; H, 2.75%; N, 3.82% Found: C, 16.19%; H, 2.72%; N, 3.79%

EXAMPLE 6

A mixture of N,N-bis(phosphonomethyl)glycine (13.2 grams, 0.05 moles), glacial acetic acid (75 mls.) and 30% hydrogen peroxide (40 mls., 0.35 moles) was stirred at room temperature for approximately 48 hours. During this period, the heterogeneous mixture became a clear, colorless solution. The solution was concentrated at reduced pressure (5 Torr) on a warm water bath. Water (100 ml.) was added to the syrupy residue and the solution was again concentrated to a viscous syrup. This syrup was then further concentrated at 50° C. at 10 Torr until a thick porous white gummy residue was obtained. The gummy residue was then concentrated at 0.2 Torr overnight, yielding a white porous powder (14.7 grams). This white solid was identified by infrared and nuclear magnetic resonance spectra analysis as N,N-bis(phosphonomethyl)glycine-N-oxide-monohydrate, and had a melting point of 65°-75° C. with decomposition. This white solid gave the following analysis:

Calculated: C, 16.17%; H, 4.41%; N, 4.71%; P, 20.85% Found: C, 16.31%; H, 4.11%; N, 4.66%; P, 20.78%

EXAMPLE 7

N-ethyl-N-phosphonomethyl glycine (3.94 grams, 0.02 moles) was charged into a reaction vessel and slurried with 30 mls. of glacial acetic acid and then heated to 68° C. Hydrogen peroxide (30%, 4.5 grams, 0.04 moles) was added dropwise over a period of 45 minutes, during which time the solid had completely dissolved. The mixture was heated at 63°-70° C. for an additional 3 hours, allowed to cool to room temperature and the acetic acid evaporated off. A viscous syrup was obtained which had a hard crystal layer on the bottom. The syrup was treated with 25 mls. of absolute ethanol and a gum precipitated. The ethanol was decanted and the residue placed in a vacuum desiccator over phosphorous pentoxide overnight, yielding a hard, brittle crystalline material. A nuclear magnetic resonance spectra analysis of this material indicated that it was a mixture of starting material and the N-oxide of N-ethyl-N-phosphonomethyl glycine. A portion of this product (2.5 grams) was dissolved in about 15 mls. of glacial acetic acid, heated to 63° C. and 4.5 grams of 30% hydrogen peroxide added dropwise over a 30 minute period. The temperature was maintained at 63°-69° C. for 10 hours, allowed to cool, filtered to yield a white solid residue having a melting point of 145°-147° C.

with decomposition. This white crystalline material was identified as N-ethyl-N-phosphonomethyl glycine-N-oxide by nuclear magnetic resonance spectra analysis:

Calculated: C, 28.18%; H, 5.68%; N, 6.57% Found: C, 27.92%; H, 5.58%; N, 6.44%

EXAMPLE 8

N-n-propyl-N-phosphonomethyl glycine (6.34 grams, 0.03 moles) and glacial acetic acid (30 mls.) were charged into a reaction vessel and stirred. The mixture was heated to 70° C. and 30% hydrogen peroxide (17.0 grams, 0.15 moles) was added dropwise over a 3¾ hour period. The temperature was maintained at 55°–70° C. for a total of 10 hours. The reaction mixture was allowed to cool and gave a positive starch-KI test. The reaction mixture was allowed to evaporate in a hood and then a stream of sulfur dioxide passed into the solution to reduce the excess hydrogen peroxide. The solution was then concentrated by passing a stream of nitrogen over the liquid. A hard crystalline crust had formed on the bottom of the syrupy liquid. The crust was broken and slurried and the mass solidified to yield a white solid. This white solid was triturated with 15 mls. of ethanol and filtered to yield a fine white powder. The white powder was air dried and had a melting point of 138°–139° C. Nuclear magnetic resonance spectra analysis and chemical analysis indicated the material to be N-n-propyl-N-phosphonomethyl glycine N-oxide.

Calculated: C, 31.72%; H, 6.21%; N, 6.17% Found: C, 31.45%; H, 6.07%; N, 5.98%

Following the above procedure, but substituting the appropriate N-substituted-N-phosphonomethyl glycine for the starting material, the following compounds were prepared:

N-isopropyl-N-phosphonomethylglycine N-oxide (m.p. 136°–137° C. with decomposition)

N-benzyl-N-phosphonomethyl glycine N-oxide (m.p. 148°–150° C. with decomposition)

N-3,4-dichlorobenzyl-N-phosphonomethyl glycine N-oxide (m.p. 135°–136° C. with decomposition)

N-sec-butyl-N-phosphonomethyl glycine N-oxide, trisodium salt trihydrate (m.p. 140°–145° C. with decomposition)

N-isobutyl-N-phosphonomethyl glycine N-oxide, trisodium salt trihydrate (m.p. 145°–147° C. with decomposition)

N-cyclohexyl-N-phosphonomethyl glycine N-oxide, trisodium salt dihydrate (m.p. > 290° C.)

N-phenethyl-N-phosphonomethyl glycine N-oxide-trisodium salt dihydrate (m.p. > 290° C.)

N-dodecyl-N-phosphonomethyl glycine, N-oxide trisodium salt dihydrate (m.p. > 280° C.)

EXAMPLE 9

The dibutyl ester of N-phosphonomethylimino diacetic acid (8.5 grams) was dissolved in 40 ml. of glacial acetic acid and charged into a suitable reactor. Hydrogen peroxide (10 ml. 30%, 0.088 mole) was added and the reaction mixture allowed to stand at room temperature for about 20 hours. A portion of the colorless solution was concentrated at 50° C. and 20 Torr and the residue diluted with diethyl ether. After the cloudy mixture became clear, the ether solution was decanted from the precipitated gum. The gum was washed with ether and then concentrated at 50° C. and 20 Torr. The residue, a white solid, was triturated with tetrahydrofuran and filtered. The tetrahydrofuran insoluble material was identified as dibutyl-N-phosphonomethylimino diacetate N-oxide and had a melting point of 111°–113° C.

Other compounds of the present invention that can be made in accordance with the procedures of the foregoing Examples include:

N-chloroethyl-N-phosphonomethylglycine-N-oxide

N-dichloropropyl-N-phosphonomethylglycine-N-oxide

N-carboxypropyl-N-phosphonomethylglycine-N-oxide

N-carboxybutyl-N-phosphonomethylglycine-N-oxide

N-carbethoxyethyl-N-phosphonomethylglycine-N-oxide

N-2-pyridylmethyl-N-phosphonomethylglycine-N-oxide

N-dichlorobenzyl-N-phosphonomethylglycine-N-oxide

N-dibromophenylethyl-N-phosphonomethylglycine-N-oxide

N-octyl-N-phosphonomethylglycine-N-oxide

Monopyridine salt of N-methyl-N-phosphonomethylglycine-N-oxide

Monobutylamine salt of N-ethyl-N-phosphonomethylglycine-N-oxide

Mono-(trimethylamine) salt of N-sec-butyl-N-phosphonomethylglycine-N-oxide

Monopyrrolidine salt of N-propyl-N-phosphonomethylglycine-N-oxide

Mono(diethylenetriamine) salt of N-ethyl-N-phosphonomethylglycine-N-oxide

Mono(isopropylamine) salt of N-methyl-N-phosphonomethylglycine-N-oxide

Mono-n-propylamine salt of N-ethyl-N-phosphonomethylglycine-N-oxide

N-2-morpholinyl-ethyl-N-phosphonomethylglycine-N-oxide

Mono(dipropargylamine) salt of N-hexyl-N-phosphonomethylglycine-N-oxide

Monosodium salt of ethyl-N-methyl-N-phosphonomethylglycinate-N-oxide

Potassium salt of ethyl-N-propyl-N-phosphonomethylglycinate-N-oxide

Mono(diallylamine) salt of N-methyl-N-phosphonomethylglycine-N-oxide

Monolithium salt of N-ethyl-N-phosphonomethylglycine-N-oxide

Monosodium salt of N-propyl-N-phosphonomethylglycine-N-oxide

Monosodium salt of N-methyl-N-phosphonomethylglycine-N-oxide

Monosodium salt of N-chloroethyl-N-phosphonomethylglycine-N-oxide

Monosodium salt of N-hexyl-N-phosphonomethylglycine-N-oxide

Monopotassium salt of N-methyl-N-phosphonomethylglycine-N-oxide

Monopotassium salt of N-propyl-N-phosphonomethylglycine-N-oxide

Monopotassium salt of N-butyl-N-phosphonomethylglycine-N-oxide

Monopotassium salt of N-hexyl-N-phosphonomethylglycine-N-oxide

Monopotassium salt of N-chloroethyl-N-phosphonomethylglycine-N-oxide

N-3-Carboxybenzyl-N-phosphonomethylglycine-N-oxide

N-4-Cyanobenzyl-N-phosphonomethylglycine-N-oxide

N-4-Nitrobenzyl-N-phosphonomethylglycine-N-oxide

N-4-Ethoxybenzyl-N-phosphonomethylglycine-N-oxide

N-3-Carbethoxybenzyl-N-phosphonomethylglycine-N-oxide

Di(n-propylamine) salt of N-pentyl-N-phosphonomethylglycine-N-oxide

Di(iso-propylamine) salt of N-butyl-N-phosphonomethylglycine-N-oxide

Di(morpholine) salt of N-propyl-N-phosphonomethylglycine-N-oxide

Mono(oleylamine) salt of N-ethyl-N-phosphonomethylglycine-N-oxide

Mono(stearylamine) salt of N-methyl-N-phosphonomethylglycine-N-oxide

Mono(methylbutylamine) salt of N-decyl-N-phosphonomethylglycine-N-oxide

N-phenoxyethyl-N-phosphonomethylglycine-N-oxide sodium salt

N-chloropropyl-N-phosphonomethylglycine-N-oxide

N-phenylpropyl-N-phosphonomethylglycine-N-oxide

N-methoxyethyl-N-phosphonomethylglycine-N-oxide

N-2,4-dimethylbenzyl-N-(phosphonomethyl)glycine-N-oxide

N-ethoxyethyl-N-(phosphonomethyl)glycine-N-oxide monoethylamine salt

N-trichlorobutyl-N-(phosphonomethyl)glycine-N-oxide

N-dibromohexyl-N-(phosphonomethyl)glycine-N-oxide

N-trifluoromethylphenethyl-N-(phosphonomethyl)glycine-N-oxide

N-3,4-dichlorobenzyl-N-(phosphonomethyl)glycine-N-oxide

Dibutylamine salt of N-dodecyl-N-(phosphonomethyl)glycine-N-oxide

N-octadecyl-N-(phosphonomethyl)glycine-N-oxide

N-methoxybutyl-N-(phosphonomethyl)glycine-N-oxide

Ethylenediamine salt of N-methyl-N-(phosphonomethyl)glycine-N-oxide

N-pyrrolidyl-ethyl-N-(phosphonomethyl)glycine-N-oxide

Dipropanolamine salt of methyl-N-(phosphonomethyl)glycine-N-oxide

N-chlorobutyl-N-(phosphonomethyl)glycine-N-oxide

N-phenoxyethyl-N-(phosphonomethyl)glycine-N-oxide

N-(N,N-diethylaminoethyl)-N-(phosphonomethyl)glycine-N-oxide

EXAMPLE 10

A mixture of N-phosphonomethylimino diacetic acid (1.0 gram), trifluoroacetic acid (20 ml. of 50% aqueous) and m-chloroperoxybenzoic acid (2.7 grams, 85% pure) were charged into a glass reactor and stirred at room temperature for 3 hours. The mixture was then heated to 60°–65° C. for 2 hours during which time the mixture became clear and then a white solid precipitated. The white solid was removed by centrifuging and was assumed to be m-chlorobenzoic acid. A portion of the clear solution was subjected to nuclear magnetic spectra analysis and was found to contain essentially pure N-phosphonomethylimino diacetic acid-N-oxide.

When peracetic acid (40%) was substituted for the chloro perbenzoic acid in this reaction and aqueous trifluoroacetic acid employed as a solvent, at from 25° C. to 70° C., the N-oxide product was identified in the reaction mixture by nuclear magnetic resonance spectra analysis.

When sodium perborate was employed in a basic aqueous media at 50° C. as the oxidizing agent in this reaction, the N-oxide product was identified in the reaction mixture by nuclear magnetic resonance spectra analysis.

When potassium persulfate was employed in a basic aqueous media at 46° C. or below, as the oxidizing agent in this reaction, the N-oxide product was identified in the reaction mixture by nuclear magnetic resonance spectra analysis.

Following the procedures described in the preceding examples, but substituting the appropriate N-substituted starting material, the following additional compounds were prepared:

N-allyl-N-phosphonomethyl glycine N-oxide, trisodium salt tetrahydrate (m.p. > 290° C.)

N-phenoxyethyl-N-phosphonomethyl glycine-N-oxide, trisodium salt monohydrate (m.p. > 290° C.)

Ethyl N,N-diphosphonomethyl glycinate N-oxide (m.p. 91°–95° C. with decomposition)

N-phosphonomethylimino diacetic acid N-oxide, diethyl ester (m.p. 105°–106° C. with decomposition)

N-phosphonomethylimino diacetic acid N-oxide, octyl ester (m.p. 99°–104° C. with decomposition)

EXAMPLE 11

The post-emergence herbicidal activity of various compounds of this invention is demonstrated as follows. The active ingredients are applied in spray form to 14 or 21 day old specimens (as indicated) of various plant species. The spray, a water or organic solvent-water solution containing active ingredient and a surfactant (35 parts butylamine salt of dodecylbenzenesulfonic acid and 65 parts tall oil condensed with ethylene oxide in the ratio of 11 moles ethylene oxide to 1 mole tall oil), is applied to the plants in different sets of pans at several rates (pounds per acre) of active ingredient. The treated plants are placed in a greenhouse and the effects are observed and recorded after approximately 2 weeks or approximately 4 weeks, as is indicated in the last column of Tables I and II.

The post-emergence herbicidal activity index used in Tables I and II is as follows:

| PLANT RESPONSE | INDEX |
| --- | --- |
| No injury | 0 |
| Slight injury | 1 |
| Moderate injury | 2 |
| Severe injury | 3 |
| Killed | 4 |

TABLE I

| Compound | Rate LB/Acre | Canada Thistle | Cocklebur | Velvet leaf | Morning-glory | Lambs quarters | Smartweed | Nutsedge | Quackgrass | Johnsongrass | Bromus Tectorum | Barnyard Grass | Observed Weeks After Treatment |
| --- | --- | --- | --- | --- | --- | --- | --- | --- | --- | --- | --- | --- | --- |
| I | 4 | 4 | 3 | 3 | 3 | 4 | — | 4 | 4 | — | 3 | 3 | 2 |
|  | 4 | 4 | 3 | 3 | 4 | — | 4 | 4 | — | 4 | 4 | 4 |
| II | 4 | 1 | 1 | 1 | 2 | 1 | 0 | 1 | 1 | 0 | 0 | 1 | 2 |

TABLE I-continued

| Compound | Rate LB/Acre | Canada Thistle | Cocklebur | Velvet leaf | Morning glory | Lambs quarters | Smartweed | Nutsedge | Quackgrass | Johnsongrass | Bromus Tectorum | Barnyard Grass | Observed Weeks After Treatment |
|---|---|---|---|---|---|---|---|---|---|---|---|---|---|
| | | 1 | 2 | 1 | 2 | 1 | 1 | 1 | 1 | 0 | 0 | 1 | 4 |
| | 10 | 1 | 4 | 1 | 2 | 3 | 2 | 1 | 2 | 1 | 2 | 2 | 2 |
| | | 2 | 4 | 3 | 2 | 4 | 3 | 3 | 4 | 3 | 3 | 3 | 4 |
| III | 4 | 1 | 2 | 3 | 2 | 4 | 3 | 1 | 3 | 2 | 2 | 3 | 2 |
| | | 2 | 4 | 3 | 2 | 4 | 4 | 2 | 4 | 3 | 3 | 4 | 4 |
| | 10 | 4 | 3 | 3 | 2 | 4 | 3 | 2 | 3 | 2 | 3 | 3 | 2 |
| | | 4 | 4 | 4 | 3 | 4 | 4 | 2 | 4 | 3 | 4 | 4 | 4 |
| IV | 4 | 1 | 1 | 2 | 2 | 0 | 3 | 1 | 1 | 2 | 3 | 2 | 2 |
| | | 1 | 1 | 2 | 2 | 0 | 4 | 2 | 1 | 3 | 2 | 2 | 4 |
| V | 4 | 3 | 3 | 3 | 3 | 3 | 2 | 2 | 4 | 4 | 3 | 4 | 2 |
| | | 4 | 4 | 3 | 3 | 3 | 4 | 2 | 4 | 4 | 4 | 4 | 4 |
| | 10 | 3 | 4 | 3 | 3 | 4 | 3 | 4 | 4 | 3 | 3 | 4 | 2 |
| | | 4 | 4 | 4 | 3 | 4 | 4 | 4 | 4 | 3 | 4 | 4 | 4 |
| VI | 4 | 3 | 1 | 3 | 2 | 3 | 4 | 2 | 3 | 3 | 2 | 4 | 2 |
| | | 4 | 2 | 3 | 2 | 3 | 4 | 2 | 4 | 3 | 3 | 4 | 4 |
| VII | 4 | 3 | 4 | 3 | 3 | 3 | — | 3 | 3 | 3 | 3 | 4 | 2 |
| | | 3 | 4 | 3 | 3 | 3 | — | 3 | 3 | 4 | 3 | 4 | 4 |
| VIII | 4 | 2 | 3 | 1 | 2 | 4 | 4 | 1 | 3 | 3 | 1 | 3 | 2 |
| | | 2 | 3 | 1 | 2 | 4 | 4 | 2 | 4 | 4 | 1 | 3 | 4 |
| IX | 4 | 3 | 3 | 3 | 3 | 4 | 3 | 3 | 3 | 3 | 3 | 4 | 2 |
| | | 4 | 4 | 3 | 3 | 4 | 4 | 4 | 4 | 4 | 4 | 4 | 4 |
| X | 4 | 4 | 3 | 2 | 2 | 4 | — | 2 | 4 | 3 | 2 | 4 | 2 |
| | | 4 | 3 | 2 | 2 | 4 | — | 3 | 4 | 3 | 2 | 4 | 4 |
| XI | 4 | 2 | 2 | 1 | 1 | 4 | 2 | 2 | 2 | 3 | 1 | 3 | 2 |
| | | 2 | 2 | 1 | 2 | 4 | 3 | 3 | 3 | 4 | 4 | 4 | 4 |
| XII | 4 | 1 | 4 | 0 | 1 | 4 | 1 | 2 | 2 | 3 | 1 | 3 | 2 |
| | | 2 | 4 | 0 | 2 | 4 | 1 | 3 | 4 | 4 | 2 | 3 | 4 |
| | 10 | 3 | 4 | 3 | 3 | 4 | 2 | 1 | 2 | 3 | 1 | 3 | 2 |
| | | 4 | 4 | 3 | 3 | 4 | 4 | 3 | 4 | 4 | 4 | 3 | 4 |
| XIII | 4 | 2 | 0 | 0 | 1 | 4 | 2 | 0 | 3 | 1 | 1 | 1 | 2 |
| | | 2 | 0 | 0 | 1 | 4 | 4 | 1 | 4 | 1 | 2 | 2 | 4 |
| | 10 | 2 | 2 | 1 | 1 | 4 | 3 | 1 | 2 | 3 | 1 | 3 | 2 |
| | | 3 | 4 | 1 | 1 | 4 | 4 | 2 | 4 | 3 | 4 | 4 | 4 |
| XIV | 4 | 3 | 3 | 2 | 1 | 2 | 3 | 3 | 3 | 3 | 4 | 3 | 2 |
| | | 3 | 4 | 4 | 2 | 3 | 4 | 3 | 4 | 3 | 4 | 4 | 4 |
| | 10 | 4 | 4 | 4 | 3 | 3 | 3 | 4 | 4 | 4 | 4 | 3 | 2 |
| XV | 4 | 1 | 1 | 1 | 1 | 0 | 0 | 1 | 3 | 2 | 1 | 1 | 2 |
| | | 2 | 2 | 0 | 1 | 2 | 2 | 1 | 4 | 3 | 2 | 2 | 4 |
| | 10 | 2 | 2 | 2 | 2 | 2 | 1 | 0 | 3 | 3 | 2 | 2 | 2 |
| | | 2 | 2 | 3 | 2 | 3 | 1 | 1 | 3 | 4 | 4 | 3 | 4 |
| XVI | 4 | 2 | 3 | 2 | 1 | 3 | 1 | 2 | 2 | 2 | 3 | 3 | 2 |
| | | 2 | 4 | 2 | 2 | 3 | 2 | 2 | 4 | 3 | 4 | 4 | 4 |
| | 10 | 3 | 3 | 2 | 1 | 4 | 3 | 2 | 2 | 3 | 3 | 4 | 2 |
| | | 4 | 4 | 3 | 2 | 4 | 4 | 3 | 4 | 4 | 4 | 4 | 4 |
| XVII | 4 | 0 | 1 | 0 | 1 | 1 | 1 | 0 | 1 | 1 | 1 | 1 | 2 |
| | | 2 | 1 | 0 | 1 | 4 | 1 | 1 | 2 | 1 | 1 | 2 | 4 |
| | 10 | 2 | 2 | 1 | 1 | 4 | 2 | 0 | 1 | 1 | 1 | 2 | 2 |
| | | 2 | 2 | 1 | 2 | 4 | 2 | 2 | 2 | 3 | 4 | 3 | 4 |
| XVIII | 4 | 0 | 0 | 0 | 1 | 0 | 0 | 0 | 0 | 0 | 0 | 0 | 2 |
| | 10 | 0 | 1 | 0 | 1 | 0 | 0 | — | 0 | 1 | 0 | 0 | 4 |
| XIX | 4 | 1 | 1 | 0 | 1 | 3 | 1 | 1 | 2 | 2 | 1 | 2 | 2 |
| | | 2 | 1 | 1 | 2 | 3 | 4 | 2 | 4 | 3 | 1 | 3 | 4 |
| | 10 | 4 | 3 | 1 | 1 | 4 | 2 | 2 | 3 | 4 | 4 | 3 | 2 |
| | | 4 | 4 | 2 | 2 | 4 | 2 | 3 | 4 | 4 | 4 | 4 | 4 |
| XX | 4 | 1 | 0 | 0 | 1 | 0 | 0 | 0 | 0 | 1 | 0 | 0 | 2 |
| | 10 | 1 | 1 | 0 | 1 | 4 | 1 | 0 | 2 | 1 | 2 | 2 | 2 |
| | | 1 | 1 | 0 | 2 | 4 | 2 | 2 | 3 | 3 | 1 | 2 | 4 |
| XXI | 4 | 2 | 2 | 1 | 1 | 3 | 2 | 1 | 1 | 3 | 2 | 3 | 2 |
| | | 2 | 4 | 0 | 1 | 3 | 1 | 2 | 2 | 3 | 1 | 4 | 4 |
| | 1 | 1 | 0 | 0 | 1 | 4 | 0 | 0 | 2 | 1 | 2 | 2 | 2 |
| | | 2 | 0 | 0 | 1 | 4 | 0 | 0 | 4 | 2 | 2 | 2 | 4 |
| XXII | 10 | 0 | 0 | 0 | 0 | 0 | 0 | 0 | 0 | 0 | 0 | 0 | 2 |
| | | 0 | 0 | 0 | 2 | 3 | 0 | 1 | 0 | 1 | 0 | 1 | 4 |
| XXIII | 4 | 2 | 2 | 2 | 2 | 4 | 2 | 0 | 3 | 2 | 2 | 4 | 2 |
| | 4 | 2 | 4 | 2 | 2 | 4 | 2 | 1 | 4 | 2 | 4 | 4 | 4 |
| | 1 | 1 | 1 | 1 | 1 | 4 | 4 | 0 | 2 | 2 | 0 | 3 | 2 |
| | 1 | 1 | 1 | 1 | 1 | 4 | 4 | 1 | 3 | 2 | 0 | 4 | 4 |
| XXIV | 20 | 1 | 1 | 0 | 1 | 1 | 1 | — | 0 | 0 | 0 | 0 | 2 |
| | 20 | 2 | 2 | 1 | 1 | 2 | 1 | — | 0 | 1 | 2 | 2 | 4 |
| XXV | 4 | 3 | 2 | 2 | 1 | 1 | 1 | 1 | 2 | 1 | 1 | 2 | 2 |
| | 4 | 4 | 3 | 2 | 2 | 1 | 4 | 0 | 4 | 2 | 2 | 2 | 4 |
| XXVI | 4 | 4 | 3 | 4 | 3 | 4 | 4 | — | 3 | 3 | 3 | 4 | 2 |
| | 4 | 4 | 3 | 4 | 3 | 4 | 4 | — | 4 | 3 | 4 | 4 | 4 |
| | 1 | 4 | 4 | 3 | 2 | 4 | 3 | 2 | 1 | 1 | 2 | 3 | 2 |
| | 1 | 4 | 4 | 3 | 2 | 4 | 4 | 3 | 1 | 1 | 3 | 4 | 4 |
| XXVII | 4 | 0 | 2 | 2 | 2 | 4 | 1 | 2 | 3 | 1 | 3 | 3 | 2 |
| | 4 | 2 | 2 | 2 | 2 | 4 | 1 | 2 | 3 | 2 | 4 | 4 | 4 |
| XXVIII | 4 | 1 | 2 | 3 | 3 | 2 | 2 | 0 | 3 | 2 | 3 | 3 | 2 |
| | 4 | 2 | 2 | 3 | 4 | 3 | 4 | 3 | 4 | 4 | 4 | 3 | 4 |

*Compounds I-X applied to 3-week old plants, other Compounds to 2-week old plants.

The compounds employed in Table I are as follows:

| COMPOUND | COMPOUND NAME |
|---|---|
| I | N-phosphonomethylimino diacetic acid-N-oxide |
| II | N,N-diphosphonomethyl glycine-N-oxide-monomethylate |
| III | N-phosphonomethylimino diacetic acid-N-oxide monosodium salt dihydrate |
| IV | N,N-diphosphonomethyl glycine-N-oxide-monohydrate |
| V | N-methyl-N-phosphonomethylglycine-N-oxide |
| VI | N-phosphonomethylimino diacetic acid-N-oxide disodium salt dihydrate |
| VII | N-phosphonomethylimino diacetic acid-N-oxide trisodium salt dihydrate |
| VIII | N-phosphonomethylimino diacetic acid-N-oxide tetrasodium salt dihydrate |
| IX | N-phosphonomethylimino diacetic acid-N-oxide monoisopropylammonium salt |
| X | N-phosphonomethylimino diacetic acid-N-oxide diethylester hydrochloride |
| XI | N-phosphonomethyliminodiacetic acid-N-oxide-dihydrate tetralithium salt |
| XII | N-phosphomethyl-N-propyl glycine, N-oxide |
| XIII | N-phosphonomethyl-N-isopropylglycine, N-oxide |
| XIV | N-phosphonomethyl-N-ethyl glycine, N-oxide |
| XV | N-phosphonomethyl-N-benzyl glycine, N-oxide |
| XVI | N-methyl-N-phosphonomethyl glycine N-oxide trisodium salt dihydrate |
| XVII | N-phosphonomethyl-N-3,4-dichlorobenzyl glycine N-oxide |
| XVIII | N-sec.-butyl-N-phosphonomethyl glycine N-oxide trisodium salt trihydrate |
| XIX | N-isobutyl-N-phosphonomethyl glycine N-oxide trisodium salt trihydrate |
| XX | N-cyclohexyl-N-phosphonomethyl glycine N-oxide trisodium salt dihydrate |
| XXI | N-phenethyl-N-phosphonomethyl glycine N-oxide trisodium salt dihydrate |
| XXII | N-dodecyl-N-phosphonomethylglycine, N-oxide, trisodium salt, dihydrate |
| XXIII | N-allyl-N-phosphonomethyl glycine N-oxide, trisodium salt tetrahydrate |
| XXIV | N-phenoxyethyl-N-phosphonomethyl glycine N-oxide, trisodium salt monohydrate |
| XXV | Ethyl N,N-diphosphonomethyl glycinate N-oxide |
| XXVI | N-phosphonomethylimino diacetic acid N-oxide, diethyl ester |
| XXVII | N-phosphonomethylimino diacetic acid N-oxide, octyl ester |
| XXVIII | N-phosphonomethylimino diacetic acid, N-oxide, dibutyl ester |

The plant species utilized in Table II are identified by letter in accordance with the following legend:

TABLE II

| | | | | | | | |
|---|---|---|---|---|---|---|---|
| A | Soybean | F | Cocklebur | L | Velvetleaf | | |
| B | Sugar Beet | G | Wild Buckwheat | M | Bromus Tectorum | | |
| C | Wheat | H | Morningglory | N | Panicum Spp | | |
| D | Rice | I | Hemp Sesbania | O | Barnyardgrass | | |
| E | Sorghum | J | Lambsquarters | P | Crabgrass | | |

| Cmpd. | Rate LB/Acre | A | B | C | D | E | F | G | H | I | J | L | M | N | O | P | * |
|---|---|---|---|---|---|---|---|---|---|---|---|---|---|---|---|---|---|
| I | 0.1 | 0 | 1 | 2 | 0 | 3 | 1 | 1 | 2 | 1 | 2 | 1 | 2 | 1 | 2 | 2 | 2 |
| I | 0.1 | 1 | 1 | 3 | 0 | 3 | 1 | 1 | 2 | 1 | 2 | 1 | 2 | 2 | 3 | 3 | 4 |
| I | 0.2 | 0 | 0 | 3 | 3 | 2 | 1 | 1 | 1 | 2 | 3 | 0 | 1 | 2 | 2 | 3 | 2 |
| I | 0.2 | 0 | 1 | 3 | 3 | 2 | 1 | 1 | 1 | 3 | 3 | 0 | 2 | 3 | 2 | 4 | 4 |
| I | 1.0 | 3 | 4 | 3 | 3 | 3 | 2 | 2 | 2 | 3 | 3 | 3 | 2 | 4 | 3 | 3 | 2 |
| I | 1.0 | 3 | 4 | 4 | 3 | 4 | 3 | 3 | 2 | 4 | 3 | 3 | 3 | 4 | 3 | 3 | 4 |

*Observed weeks after treatment.

In Table II, the Compound was applied to 3-week old plants.

The herbicide compositions, including concentrates which require dilution prior to application to the plants, of this invention contain at least one active ingredient and an adjuvant in liquid or solid form. The compositions are prepared by admixing the active ingredient with an adjuvant including diluents, extenders, carriers and conditioning agents to provide compositions in the form of finely-divided particulate solids, pellets, solutions, dispersions or emulsions. Thus, the active ingredient can be used with an adjuvant such as a finely-divided solid, a liquid of organic origin, water, a wetting agent, a dispersing agent, an emulsifying agent or any suitable combination of these. From the viewpoint of economy and convenience, water is the preferred diluent, particularly with the highly water-soluble salts such as the alkali metal salts and amine and ammonium salts.

The herbicide compositions of this invention, particularly liquids and soluble powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent" it is understood that wetting agents, dispersing agents, suspending agents and emulsying agents are included therein. Anionic, cationic and non-ionic agents can be used with equal facility.

Preferred wetting agents are alkyl benzene and alkyl naphthalene sulfonates, sulfated fatty alcohols, amines or acid amides, long chain acid esters of sodium isethionate, esters of sodium sulfosuccinate, sulfated or sulfonated fatty acid esters, petroleum sulfonates, sulfonated vegetable oils, polyoxyethylene derivatives of alkylphenols (particularly isooctylphenol and nonylphenol) and polyoxyethylene derivatives of the mono-higher fatty acid esters of hexitol anhydrides (e.g. sorbitan). Preferred dispersants are methyl cellulose, polyvinyl alcohol, sodium lignin sulfonates, polymeric alkyl naphthalene sulfonates, sodium naphthalene sulfonate, polymethylene bisnaphthalenesulfonate and sodium N-methyl-N-(long chain acid) taurates.

Water-dispersible powder compositions can be made containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The water-dispersible powder of this invention usually contains from about 5 to about 95 parts by weight of active ingredient, from about 0.25 to 25 parts by weight of wetting agent, from about 0.25 to 25 parts by weight of dispersant and from 4.5 to about 94.5 parts by weight of inert solid extender, all parts being by weight of the total composition. Where required, from about 0.1 to 2.0 parts by weight of the solid inert extender can be replaced by a corrosion inhibitor or anti-foaming agent or both.

Aqueous suspensions can be prepared by mixing together and grinding an aqueous slurry of water-insoluble active ingredient in the presence of dispersing agents to obtain a concentrated slurry of very finely-divided particles. The resulting concentrated aqueous suspension is characterized by its extremely small particle size, so that when diluted and sprayed, coverage is very uniform.

Emulsifiable oils are usually solutions of active ingredient in water-immiscible or partially water-immiscible solvents together with a surface active agent. Suitable solvents for the active ingredient of this invention include hydrocarbons and water-immiscible ethers, esters or ketones. The emulsifiable oil compositions generally contain from about 5 to 95 parts active ingredient, about 1 to 50 parts surface active agent and about 4 to 94 parts solvent, all parts being by weight based on the total weight of emulsifiable oil.

Although the herbicidal compositions of this invention can also contain other additaments, for example fertilizers, phytotoxicants and plant growth regulants, pesticides and the like used as adjuvants or in combination with any of the above-described adjuvants, in some instances it is preferred to employ the compositions of this invention alone with sequential treatments with other phytotoxicants, fertilizers and the like for maximum effect. For example, the field could be sprayed with a composition of this invention either before or after being treated with fertilizers, other phytotoxicants and the like. The compositions of this invention can also be admixed with the other materials, e.g. fertilizers, other phytotoxicants, etc., and applied in a single application. Chemicals useful in combination with the active ingredients of this invention either simultaneously or sequentially include for example triazines, ureas, carbamates, acetamides, acetanilides, uracils, acetic acids, phenols, thiolcarbamates, triazoles, benzoic acids, nitriles and the like such as:

3-amino-2,5-dichlorobenzoic acid
3-amino-1,2,4-triazole
2-methoxy-4-ethylamino-6-isopropylamino-s-triazine
2-chloro-4-ethylamino-6-isopropylamino-s-triazine
2-chloro-N,N-diallylacetamide
2-chloroallyl diethyldithiocarbamate
N'-(4-chlorophenoxy) phenyl-N,N-dimethylurea
1,1'-dimethyl-4,4'-bipyridinium dichloride
isopropyl m-(3-chlorophenyl)carbamate
2,2-dichloropropionic acid
S-2,3-dichloroallyl N,N-diisopropylthiolcarbamate
2-methoxy-3,6-dichlorobenzoic acid
2,6-dichlorobenzonitrile
N,N-dimethyl-2,2-diphenylacetamide
6,7-dihydrodipyrido(1,2-a:2',1'-c)-pyrazidinium salt
3-(3,4-dichlorophenyl)-1,1-dimethylurea
4,6-dinitro-o-sec-butylphenol
2-methyl-4,6-dinitrophenol
ethyl N,N-dipropylthiolcarbamate 2,3,6-trichlorophenylacetic acid
5-bromo-3-isopropyl-6-methyluracil
3-(3,4-dichlorophenyl)-1-methoxy-1-methylurea
2-methyl-4-chlorophenoxyacetic acid
3-(p-chlorophenyl)-1,1-dimethylurea
1-butyl-3-(3,4-dichlorophenyl)-1-methylurea
N-1-naphthylphthalamic acid
1,1'-dimethyl-4,4'-bipyridinium salt
2-chloro-4-bis(isopropylamino)-s-triazine
2-chloro-4,6-bis(ethylamino)-s-triazine
2,4-dichlorophenyl-4'-nitrophenyl ether
α,α,α-trifluoro-2,6-dinitro-N,N-dipropyl-p-toluidine
S-propyl dipropylthiolcarbamate
2,4-dichlorophenoxyacetic acid
N-isopropyl-2-chloroacetanilide
2',6'-diethyl-N-methoxymethyl-2-chloroacetanilide monosodium acid methanearsonate disodium methanearsonate
N-(1,1-dimethylpropynyl)-3,5-dichlorobenzamide Fertilizers useful in combination with the active ingredients include for example ammonium nitrate, urea, potash, and superphosphate.

When operating in accordance with the present invention, effective amounts of the N-organo-N-phosphonomethylglycine N-oxide are applied to above ground portions of plants. The application of liquid and particulate solid herbicidal compositions to above ground portions of plants can be carried out by conventional methods, e.g., power dusters, boom and hand sprayers and spray dusters. The compositions can also be applied from airplanes as a dust or a spray because of their effectiveness at low dosages. The application of herbicidal compositions to aquatic plants is usually carried out by spraying the compositions on the aquatic plants in the area where control of the aquatic plants is desired.

The application of an effective amount of the compounds of this invention to the plant is essential and critical for the practice of the present invention. The exact amount of active ingredient to be employed is dependent upon the response desired in the plant as well as such factors as the plant species and stage of development thereof, and the amount of rainfall as well as the specific N-organo-N-phosphonomethylglycine N-oxide employed. In foliar treatment for the herbicidal control of vegetative growth, the active ingredients are applied in amounts from about 0.1 to about 20 or more pounds per acre. In applications for the control of aquatic plants, the active ingredients are applied in amounts of from about 1 part per million to about 1,000 parts per million, based on the aquatic medium. An effective amount for phytotoxic or herbicidal control is that amount necessary for overall or selective control, i.e., a phytotoxic or herbicidal amount. It is believed that one skilled in the art can readily determine from the teachings of this specification, including examples, the approximate application rate.

Although the invention is described with respect to specific modifications, the details thereof are not to be construed as limitations except to the extent indicated in the following claims.

What is claimed is:

1. A herbicidal composition comprising an inert adjuvant and an effective amount of a compound of the formula

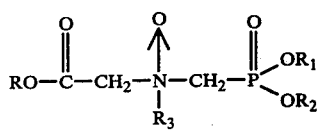

wherein $R_1$ and $R_2$ are each independently selected from the group consisting of hydrogen, salt forming alkali or alkaline earth metal cations, ammonium or organic ammonium groups, said organic ammonium group being derived from an organic amine having a molecular weight below about 300 and containing not more than two amine groups, R is selected from the same group as $R_1$ plus lower alkyl, and $R_3$ is selected from the group consisting of alkyl of 1 to 12 carbon atoms, allyl, cyclohexyl, phenalkyl and phenoxyalkyl of 7 to 8 carbon atoms, and the mono and dichloro or bromo derivatives of such alkyl, allyl, cyclohexyl, phenalkyl and phenoxyalkyl.

2. A herbicidal composition as defined in claim 1 wherein R is lower alkyl.

3. A herbicidal composition as defined in claim 1 wherein $R_3$ is alkyl of 1 to 12 carbon atoms.

4. A herbicidal composition as defined in claim 1 wherein $R_3$ is phenalkyl or phenoxyalkyl of 7 to 8 carbon atoms.

5. A herbicidal composition as defined in claim 1 wherein R, $R_1$ and $R_2$ are sodium.

6. A herbicidal composition as defined in claim 1 wherein R, $R_1$ and $R_2$ are hydrogen.

7. A herbicidal composition as defined in claim 1 wherein the compound is N-methyl-N-phosphonomethyl glycine N-oxide.

8. A herbicidal composition as defined in claim 1 wherein the compound is N-ethyl-N-phosphonomethyl glycine N-oxide.

9. A herbicidal composition as defined in claim 1 wherein the compound is N-propyl-N-phosphonomethyl glycine N-oxide.

10. A herbicidal composition as defined in claim 1 wherein the compound is N-isopropyl-N-phosphonomethyl glycine N-oxide.

11. A herbicidal composition as defined in claim 1 wherein the compound is N-sec. butyl-N-phosphonomethyl glycine N-oxide.

12. A herbicidal composition as defined in claim 1 wherein the compound is N-isobutyl-N-phosphonomethyl glycine N-oxide.

13. A herbicidal composition as defined in claim 1 wherein the compound is N-benzyl-N-phosphonomethyl glycine N-oxide.

14. A herbicidal composition as defined in claim 1 wherein the compound is N-3,4-dichlorobenzyl-N-phosphonomethyl glycine N-oxide.

15. A herbicidal composition as defined in claim 1 wherein the compound is N-cyclohexyl-N-phosphonomethyl glycine N-oxide.

16. A herbicidal composition as defined in claim 1 wherein the compound is N-allyl-N-phosphonomethyl glycine N-oxide.

* * * * *